(12) United States Patent
Anderson et al.

(10) Patent No.: US 9,470,246 B1
(45) Date of Patent: Oct. 18, 2016

(54) HYDRAULIC ACTUATION SYSTEM FOR WORK MACHINE

(71) Applicant: CNH Industrial America LLC, New Holland, PA (US)

(72) Inventors: Charles D. Anderson, Temple, TX (US); David J. Sanning, Burlington, IA (US)

(73) Assignee: CNH Industrial America LLC, New Holland, PA (US)

( * ) Notice: Subject to any disclaimer, the term of this patent is extended or adjusted under 35 U.S.C. 154(b) by 0 days.

(21) Appl. No.: 14/731,922

(22) Filed: Jun. 5, 2015

(51) Int. Cl.
| | |
|---|---|
| *F15B 11/16* | (2006.01) |
| *F15B 13/02* | (2006.01) |
| *F15B 13/06* | (2006.01) |
| *B60K 25/06* | (2006.01) |
| *B60K 17/28* | (2006.01) |
| *E02F 3/42* | (2006.01) |
| *E02F 9/22* | (2006.01) |

(52) U.S. Cl.
CPC .............. *F15B 11/163* (2013.01); *B60K 17/28* (2013.01); *B60K 25/06* (2013.01); *E02F 3/425* (2013.01); *E02F 9/22* (2013.01); *E02F 9/2225* (2013.01); *F15B 13/024* (2013.01); *F15B 13/06* (2013.01); *F15B 2211/205* (2013.01); *F15B 2211/3116* (2013.01); *F15B 2211/50* (2013.01)

(58) Field of Classification Search
CPC .... F15B 11/163; F15B 13/024; F15B 13/06; F15B 2211/3116; F15B 2211/50; F15B 2211/205; F15B 2211/50509; F15B 2211/50518; F15B 2211/50536; F15B 2211/50554; F15B 11/165; F15B 11/167; E02F 9/22; E02F 9/2225; E02F 3/425; B60K 25/06; B60K 17/28
See application file for complete search history.

(56) References Cited

U.S. PATENT DOCUMENTS

| | | | |
|---|---|---|---|
| 4,165,613 A | 8/1979 | Bernhoft et al. | |
| T986,004 I4 | 9/1979 | Stroup et al. | |
| 5,088,384 A * | 2/1992 | Lonnemo | F15B 13/02 91/461 |
| 5,413,452 A | 5/1995 | Lech et al. | |
| 5,419,129 A | 5/1995 | Becker et al. | |
| 5,873,244 A | 2/1999 | Cobo et al. | |
| 6,282,890 B1 * | 9/2001 | Takano | E02F 9/2203 60/420 |
| 7,222,484 B1 | 5/2007 | Dornbach | |
| 7,481,052 B2 | 1/2009 | Mauch et al. | |
| 8,353,157 B2 | 1/2013 | Lech et al. | |
| 8,875,506 B2 * | 11/2014 | Hennemann | E02F 9/2066 60/443 |
| 2012/0233996 A1 * | 9/2012 | Quinnell | E02F 9/2235 60/421 |
| 2013/0220425 A1 * | 8/2013 | Pomeroy | E02F 9/2235 137/1 |
| 2013/0263587 A1 | 10/2013 | Azuma et al. | |
| 2016/0138618 A1 * | 5/2016 | Gorman | F15B 11/024 60/327 |

* cited by examiner

*Primary Examiner* — Drew Brown
(74) *Attorney, Agent, or Firm* — Patrick M. Sheldrake

(57) ABSTRACT

A hydraulic system for a loader backhoe work machine in which a propulsion system has a limited output and the pressure relief for the hydraulic actuation system is at a first level for the loader function in which the machine is moved on the ground and a second higher pressure relief for when the backhoe function is being performed.

18 Claims, 2 Drawing Sheets

HYDRAULIC ACTUATION SYSTEM FOR WORK MACHINE

BACKGROUND OF THE INVENTION

1. Field of the Invention

The present invention relates to work machines, and more specifically to such machines that have hydraulic actuation systems incorporated therein.

2. Description of the Related Art

One of the most useful and popular work machines, particularly in the construction field, is a loader backhoe work machine. When operating under the loading function, machines of this type elevate, transport and unload granular material, soil or other items. In this function, the primary propulsion unit for the device is used for work machine movement along the ground, as well as powering the hydraulic actuators used to elevate and unload material. In the backhoe function, the machine is essentially stationary and the backhoe is used to penetrate the ground, removing scoops of soil and then moving it without the work machine being transported across the ground.

For certain types of lighter duty loader backhoe machines, it is desirable to use a smaller output propulsion unit. This allows the overall machine to be more cost effective and widely available for performing the loading and backhoe functions. With the smaller size propulsion unit, there is an issue when the unit is being used in the loader unit. Since the hydraulic pressure for the actuators of the loader system is provided by a pump driven off the propulsion unit, more power directed to the actuation system leaves less available for propulsion along the ground. This has a limiting factor on the usefulness of the machine for the dual functions.

Accordingly, what is needed in the art is a hydraulic actuation system for such a work machine in which the available power is effectively and economically balanced and split between the propulsion system and the actuation system.

SUMMARY OF THE INVENTION

The present invention simply and effectively provides dual levels of available power to the actuation system in a work machine of the loader backhoe design.

In one form, the invention is a hydraulic actuation system including a reservoir and a pump having an inlet fluidly connected to the reservoir for supplying pressurized fluid. A first group of at least one actuator is provided and a first group of at least one control valve for the first group of at least one actuator is fluidly connected to the pump in an open center relationship. The first group of at least one control valve is connected to operate the first group of at least one actuator. A second group of at least one actuator is provided and a second group of at least one control valve is fluidly connected to the downstream side of the first group of at least one control valve and is connected to operate the second group of at least one actuator. A pressure relief valve having first and second pressure relief levels in response to a pilot pressure is fluidly connected to the reservoir to discharge excess pressure with the pressure relief valve being fluidly connected to the output of the pump. A line fluidly connects the pressure relief valve pilot pressure to a point in the system downstream of the first group of at least one control valve and upstream of the second group of at least one control valve.

In another form, the invention includes a work machine including a frame and a propulsion unit mounted within the frame. A plurality of wheels is mounted on the frame for ground movement and a power train connects the propulsion unit to the wheels for ground movement. A hydraulic reservoir is provided on the frame and a pump driven by the propulsion unit has an inlet fluidly connected to the reservoir for supplying pressurized hydraulic fluid. A first group of at least one actuator is mounted on the frame for performing a first function. A first group of at least one control valve for the first group of at least one actuator is fluidly connected to the pump in an open center relationship and is connected to operate the first group of at least one actuator to perform a second function. A second group of at least one actuator is mounted on the frame for performing a second function. A second group of at least one control valve is fluidly connected to the downstream side of the first group of at least one control valve and is connected to operate the second group of at least one actuator. A pressure relief valve having first and second levels of pressure relief in response to a pilot pressure is fluidly connected to the reservoir to discharge excess pressure, the pressure relief valve being fluidly connected to the output of the pump. A line fluidly connects the pressure relief valve pilot pressure to a point in the system downstream of the first group of at least one control valve and upstream of the second group of at least one control valve.

An advantage of the present invention is that a dual level of hydraulic force is simply and effectively made available for different levels of power.

Another advantage is that the dual level of force may be employed without complicated hardware additions.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
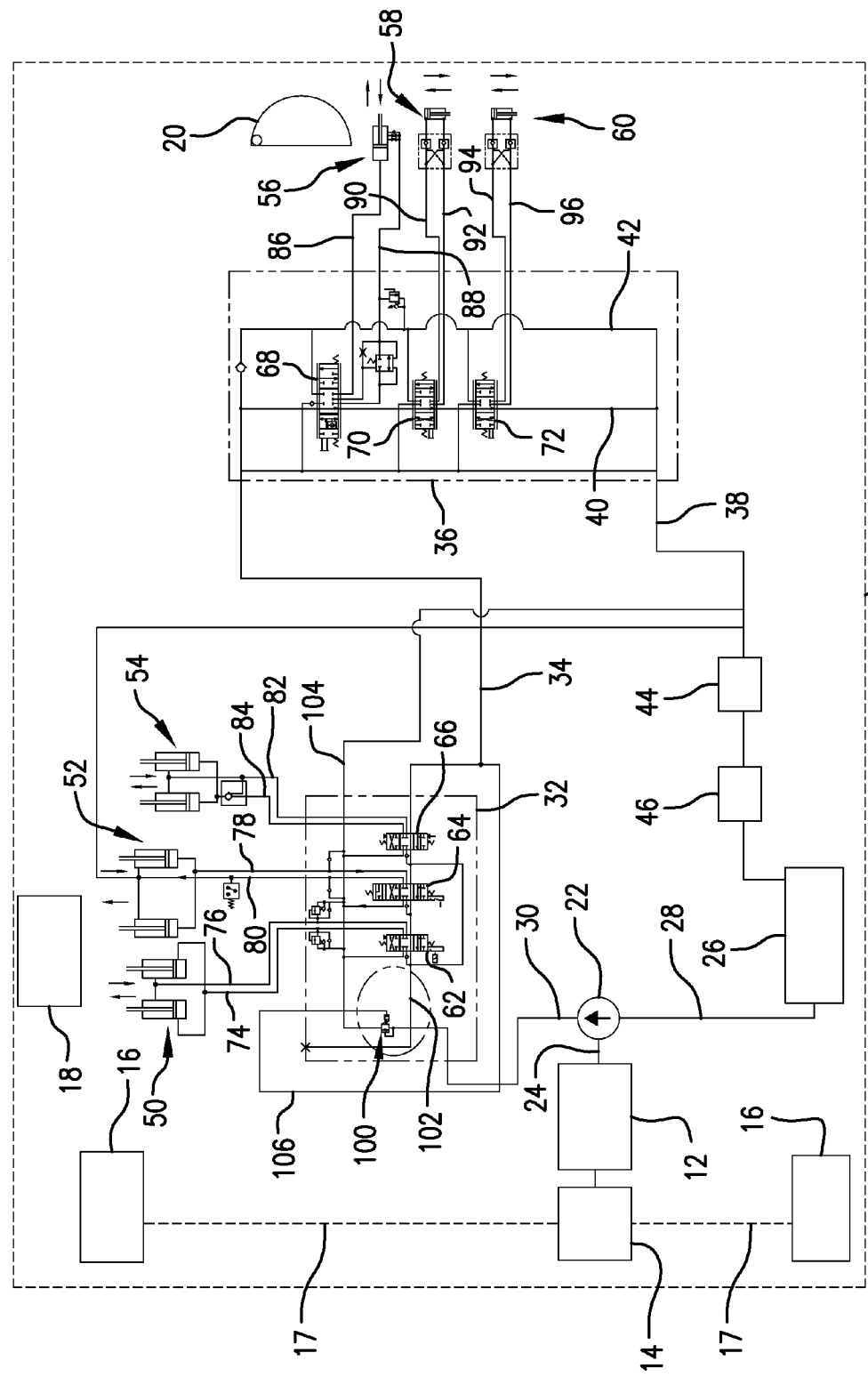
FIG. 1 is an overall schematic system of a work machine showing a hydraulic system incorporating the present invention.

Referring now to the drawings, and more particularly to FIG. 1, there is shown a work machine 10 which is illustrated as a loader backhoe machine. The work machine 10 may also be known as a TLB or tractor loader backhoe. Work machine 10 has a propulsion unit, usually in the form of a diesel engine 12, owing to its fuel economy and available torque output. A power train 14 is driven by propulsion unit 12 and in turn drives ground wheels 16, only two of which are shown, through mechanical interconnections illustrated at 17.

A loading bucket 18 is provided at the front end of the work machine 10 and a backhoe 20 is provided at the aft end of the work machine 10. Both bucket 18 and backhoe 20 are mounted on articulated arms to perform functions normally associated with these components. The details of the articulated links and mechanical interconnections are omitted to enable a clearer focus on the present invention.

The bucket 18 and backhoe 20 are manipulated through a hydraulic actuation system including a hydraulic pump 22, shown as a gear pump, driven from engine 24 by a mechanical connection and receiving hydraulic fluid from a suitable reservoir 26 through an inlet line 28. An output line 30 receives pressurized liquid from pump 22 and passes it through a valve assembly 32 controlling the bucket 18 function. An additional line 34, referred to as a power beyond line, is fluidly connected to a valve assembly 36 controlling the functions for backhoe 20. Return lines 40 and 42 from valve assembly 36 connect to main return line 38 which may extend through an appropriate filter 44 and an oil cooler 46 before delivery to reservoir 26.

Bucket 18 is acted on by actuator pairs 50, 52 and 54 in response to pressurized fluid controlled by valve assembly 32. Backhoe 20 is manipulated by actuators 56, 58 and 60 receiving inputs from valve assembly 36.

Valve assembly 32 has hydraulic control valves 62, 64 and 66 connected to have an open center hydraulic flow arrangement. The open center hydraulic flow arrangement is such that, in neutral, hydraulic fluid passes from pump 22 through line 30 through the center of valve assembly 32 and power beyond valve 34 and finally to return line 38. The valve assembly 36 includes hydraulic control valves 68, 70 and 72 controlling the actuators 56, 58 and 60. The hydraulic valve 68, 70 and 72 are shown as having an open center hydraulic system. However, they may be employed in alternate arrangements and still achieve the objects and benefits of the present invention. The control valve 62 controls flow through lines 74 and 76 which are connected to actuators 50 to extend and retract actuators 50 and thus manipulate bucket 18. Control valve 64 has output lines 78 and 80 connected to actuator pairs 52 to extend and retract those actuators and provide further manipulation of bucket 18. Hydraulic control valve 66 has output lines 82 and 84 to extend and retract actuator pairs 54 to manipulate bucket 18 in still a further fashion.

In valve assembly 36, hydraulic control valve 68 is connected to lines 86 and 88 to extend and retract actuator 56 providing one degree of manipulation of backhoe 20. Hydraulic control valve 70 has output lines 90 and 92 to extend and retract actuator 58 providing a further degree of manipulation of backhoe 20. Finally, hydraulic control valve 72 has output lines 94 and 96 extending and retracting actuator 60 to provide still another degree of manipulation for bucket 20.

In operation, the pump 22 continuously circulates fluid through the system through line 30, 34 and finally back through return line 38. When control valves 62, 64 or 66 are operated, they divert flow from main output line 30 and direct it to the appropriate actuator pairs 50, 52 or 54. Through internal hydraulic connections, the actuators 50, 52 and 54 may all be independently and jointly operated to manipulate bucket 18. However, when the valves 62, 64 or 66 are operating, the pressure in the power beyond line 34 drops to a return line pressure level. This is employed in the system since the bucket 18 and backhoe 20 are not simultaneously operated, but are, in fact, alternately operated. When the backhoe 20 is to be operated, the control valves 62, 64 and 66 are in their open center position so that pressure is available in line 34 to supply to control valves 68, 70 and 72 to operate their respective actuators 56, 58 and 60 and thus manipulate backhoe 20.

When the work machine 10 is operated as a loader during which it manipulates the bucket 18, the power train 14 also receives power from propulsion unit 12 to drive ground wheels 16 and move the work machine 10 along the ground. When the backhoe function is employed, backhoe 20 is the only component being manipulated so that greater power is available to perform the functions of a backhoe including digging into soil. When the propulsion unit 12 is capacity limited as in the case of smaller TLBs, the available power for the loader function in the hydraulic system needs to be at a lower level than that for the backhoe function. While current hydraulic systems use elaborate control systems to achieve a dual hydraulic system power level, the present invention described in FIGS. 1 and 2 does so simply effectively and with a minimum of extra components.

Figure 2:
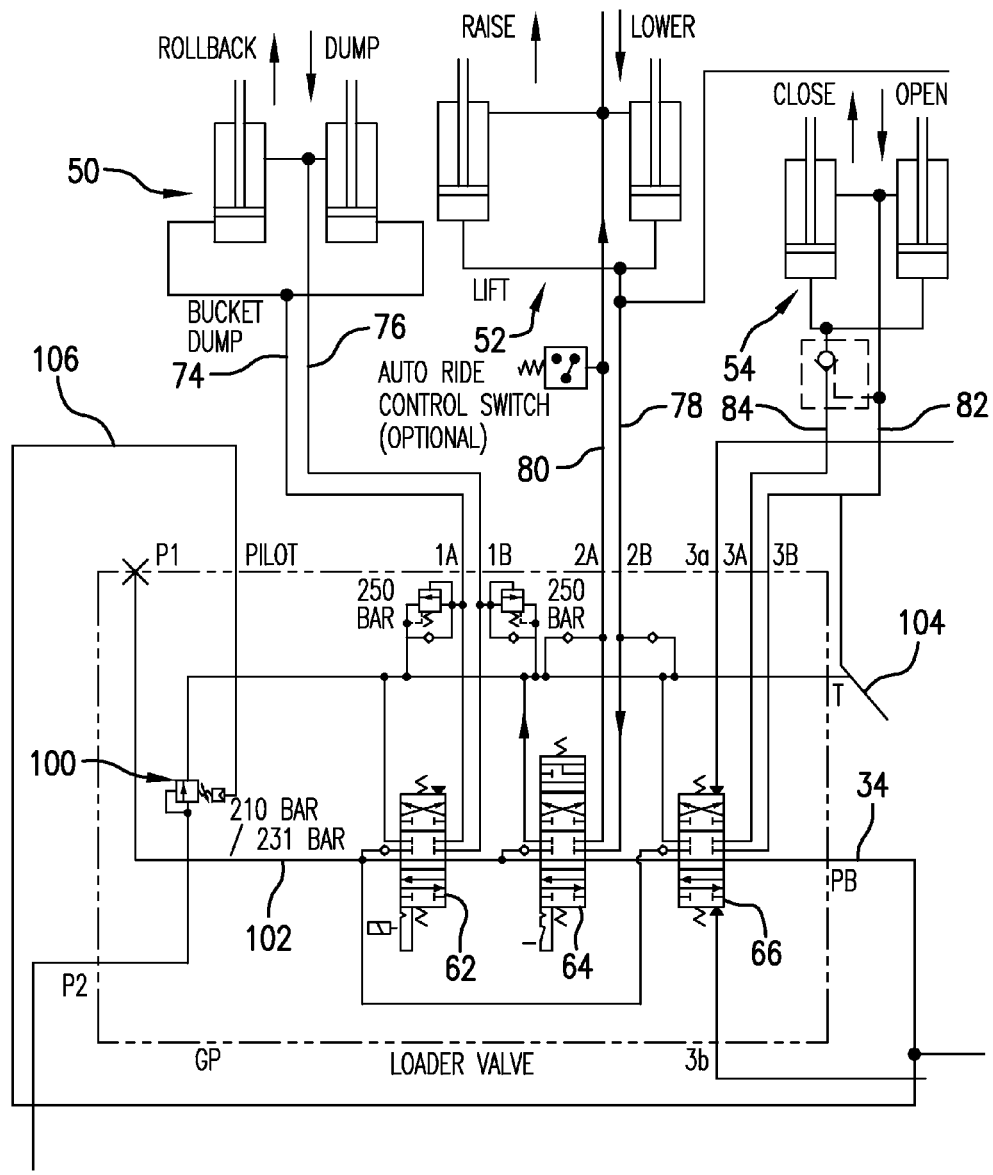
FIG. 2 is an enlarged fragmentary view of a portion of the hydraulic actuation system of FIG. 1.

Referring now to FIGS. 1 and 2, a pressure relief valve 100 is connected to line 102 passing through control valve assembly 32 and connected to line 30. Pressure relief valve 100 is set to relieve pressure in line 30 and pass it to return line 104 which is connected to the main return line 38. However, pressure relief valve 100 is one of a class of pressure relief valves having a pilot function so that in the absence of a signal on line 106 leading to pressure relief valve 100, a first, lower, pressure level is achieved, usually at a setting established by an internal spring loading. When a pressure level is detected in line 106 which extends to the power beyond line 34, the pressure relief is at a higher level owing to the additional pressure applied through line 106 to the pilot valve function. An example of a typical pressure relief setting that enables a higher loading in the presence of a pressure signal is 210 BAR for no signal and 231 BAR in the presence of a signal.

The pressure signal occurs when the control valves in valve assembly 32 are in the open center position and the control valves 68, 70 and 72 are employed to divert hydraulic fluid from output line 34 to manipulate backhoe 20. Thus, the upper limit of hydraulic pressure and thus the power and work available in the backhoe function is higher than it is for the lower function. By utilizing a simple interconnection between the pilot relief valve 100 and the power beyond line 34, a dual hydraulic power arrangement can be economically and effectively employed in the work machine 10. It should be noted that the signal shown as line 106 may be connected to a point anywhere between the last control valve 66 in valve assembly 32 and the entry to the valve assembly 36 and still achieve the same benefits. The net result of the arrangement is a smaller TLB that employs propulsion units having 55 kW output meeting a different regulatory standard, but at the same time utilizing all the available power from the propulsion unit 12 as efficiently as possible.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. A hydraulic actuation system comprising:
a reservoir for hydraulic fluid;
a pump having an inlet fluidly connected to said reservoir and supplying pressurized hydraulic fluid;
a first group of at least one actuator;

a first group of at least one control valve for said first group of at least one actuator fluidly connected to said pump in an open center relationship and connected to operate said first group of at least one actuator;

a second group of at least one actuator;

a second group of at least one control valve fluidly connected to the downstream side of said first group of at least one control valve and connected to operate said second group of at least one actuator;

a pressure relief valve having first and second levels of pressure relief in response to a pilot pressure and fluidly connected to said reservoir to discharge excess pressure, said pressure relief valve being fluidly connected to the output of said pump; and, a line fluidly connecting the pressure relief valve pilot pressure to a point in the hydraulic actuation system downstream of said first group of at least one control valve and upstream of said second group of at least one control valve.

2. The hydraulic actuation system as claimed in claim 1, wherein said pressure relief valve has a higher pressure relief level for said second group of at least one actuator.

3. The hydraulic actuation system as claimed in claim 1, having a plurality in said first group of actuators and control valves.

4. The hydraulic actuation system as claimed in claim 3, wherein there is a plurality of actuators and control valves in both first and second groups.

5. The hydraulic actuation system as claimed in claim 1, wherein said pressure relief valve is spring biased to said first level of pressure relief in the absence of a signal from said line and said second level in response to a pressure level in said line, wherein said second level is higher than said first level.

6. The hydraulic actuation system as claimed in claim 5, wherein said first pressure level is set by a spring and the second pressure level is set by said spring and a pressure signal from said line.

7. The hydraulic actuation system as claimed in claim 1, wherein said first pressure relief level is approximately 210 BAR and said second level of pressure relief is approximately 231 BAR.

8. The hydraulic actuation system as claimed in claim 1, wherein said pump is a gear pump.

9. The hydraulic actuation system as claimed in claim 1, wherein said first group of said at least one actuator is for a loader and said second group of said at least one actuator is for a backhoe.

10. A work machine comprising:
a frame;
a propulsion unit incorporated in said frame;
a plurality of ground drive wheels on said frame;
a power train connecting the output of said propulsion unit to said wheels for ground movement;
a reservoir for hydraulic fluid;

a pump driven by said propulsion unit and having an inlet fluidly connected to said reservoir and supplying pressurized hydraulic fluid;

a first group of at least one actuator mounted on said frame for a first function;

a first group of at least one control valve for said first group of at least one actuator fluidly connected to said pump in an open center relationship and connected to operated said first group of at least one actuator;

a second group of at least one actuator mounted on said frame for performing a second function;

a second group of at least one control valve fluidly connected to the downstream side of said first group of at least one control valve and connected to operate said second group of at least one actuator;

a pressure relief valve having first and second levels of pressure relief in response to a pilot pressure and fluidly connected to said reservoir to discharge excess pressure, said pressure relief valve being fluidly connected to the output of said pump; and a line fluidly connecting the pressure relief valve pilot pressure to a point in the system downstream of said first group of at least one control valve and upstream of said second group of at least one control valve.

11. The work machine as claimed in claim 10, wherein the pressure relief level for said second group of at least one actuator is a higher level than the pressure relief for said first group of at least one actuator.

12. The work machine as claimed in claim 10, having a plurality of actuators and control valves in said first group.

13. The work machine as claimed in claim 12, having a plurality of actuators and control valves in both first and second groups.

14. The work machine as claimed in claim 10, wherein said pressure relief valve has a pressure relief set by a spring for said first and lower pressure level and a pressure relief set by said spring and by pressure input from said line for said second and higher pressure level.

15. The work machine as claimed in claim 10, wherein said first pressure relief level is approximately 210 BAR and the second level of pressure relief is approximately 231 BAR.

16. The work machine as claimed in claim 10, wherein said pump is a gear pump.

17. The work machine as claimed in claim 10, wherein said first group of at least one actuator is for a loader function and the second group of said at least one actuator is for a backhoe function.

18. A work machine as claimed in claim 17, wherein said propulsion system has a given power output and said work machine requires ground movement and loader movement for said first group of at least one actuator, thus limiting the power available to said first group of at least one actuator and the pressure relief permits a higher level of hydraulic force when the backhoe function is being performed.

\* \* \* \* \*